United States Patent [19]

O'Donnell, Jr.

[11] Patent Number: 5,713,893

[45] Date of Patent: Feb. 3, 1998

[54] TEST SUBSTRATE FOR LASER EVALUATION

[76] Inventor: Francis E. O'Donnell, Jr., 709 The Hamptons La., Town & Country, Mo. 63017

[21] Appl. No.: 647,603

[22] Filed: May 13, 1996

Related U.S. Application Data

[63] Continuation-in-part of Ser. No. 410,494, Mar. 24, 1995, abandoned, which is a continuation-in-part of Ser. No. 514,806, Oct. 31, 1995, which is a continuation-in-part of Ser. No. 269,139, Jun. 30, 1994, Pat. No. 5,460,627, which is a continuation-in-part of Ser. No. 55,578, May 3, 1993, abandoned.

[51] Int. Cl.$^6$ ............................................ A61B 14/00
[52] U.S. Cl. ............................................ 606/10; 606/2; 606/5
[58] Field of Search ............................. 606/2–6, 10–14

[56] References Cited

U.S. PATENT DOCUMENTS

| | | |
|---|---|---|
| 4,461,294 | 7/1984 | Baron . |
| 4,669,466 | 6/1987 | L'Esperance . |
| 4,676,790 | 6/1987 | Kern . |
| 4,863,268 | 9/1989 | Clarke et al. . |
| 4,994,058 | 2/1991 | Raven et al. ............................ 606/5 |
| 5,163,934 | 11/1992 | Munnerlyn . |
| 5,261,822 | 11/1993 | Hall et al. . |
| 5,279,611 | 1/1994 | McDonnell et al. ..................... 606/4 |
| 5,460,627 | 10/1995 | O'Donnell, Jr. . |

OTHER PUBLICATIONS

An Atlas of Corneal Topography by Donald R. Sanders, M.D., PhD, and Douglas D. Koch, M.D. --pp. 12 through 17.

*Primary Examiner*—David M. Shay
*Attorney, Agent, or Firm*—Paul M. Denk

[57] ABSTRACT

A test substrate for the calibration of a laser used in ophthalmologic surgery. The test substrate is formed from a homogenous, relatively anhydrous material that ablates a rate approximately that of human corneal tissue. In one embodiment, the test substrate is formed from a plastic material such as acrylic or silicone. In another embodiment, the test substrate is formed from an organic gel or inorganic gel such as cross-linked collagen.

3 Claims, 5 Drawing Sheets

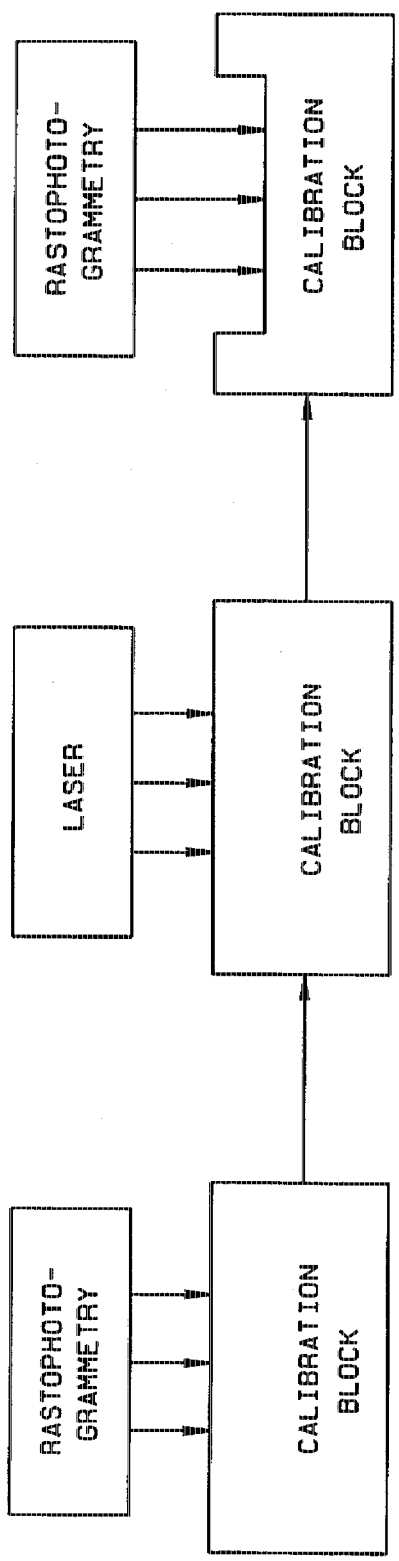
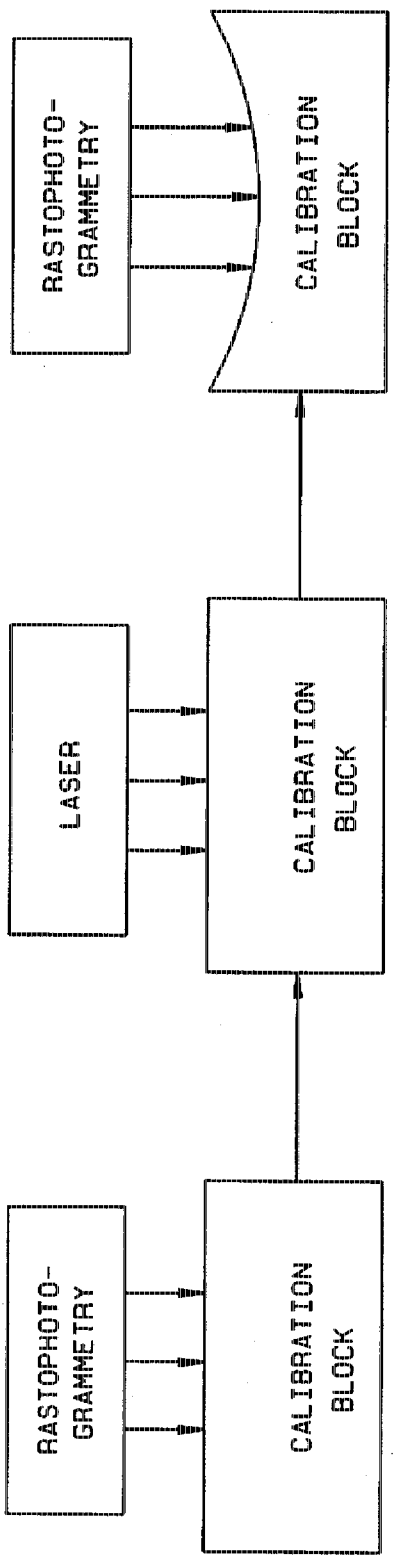
FIG. 1
FIG. 2

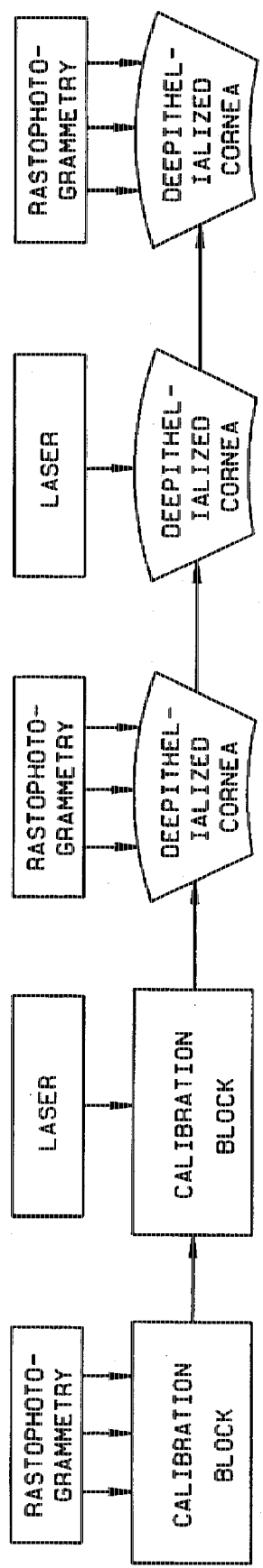
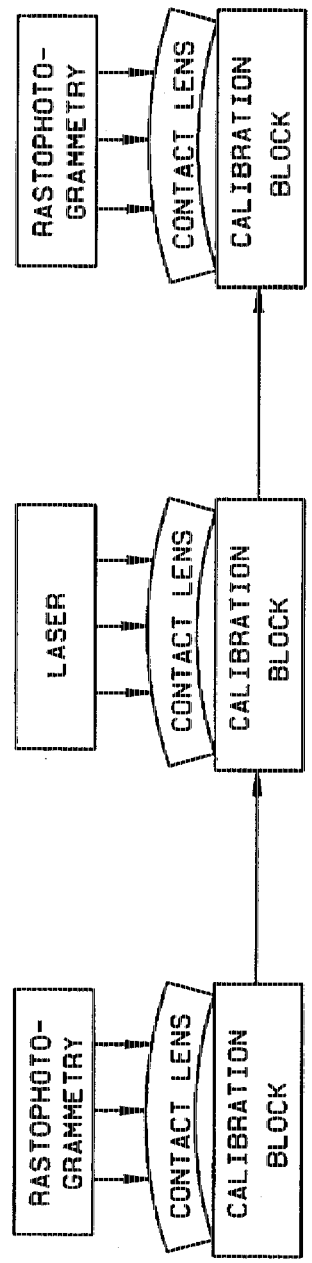
FIG. 3
FIG. 4A

TEST SUBSTRATE FOR LASER EVALUATION

CROSS-REFERENCE TO RELATED APPLICATIONS

This application is a continuation-in-part of application Ser. No. 08/410,494, filed Mar. 24, 1995; abandoned which is a continuation-in-part of Ser. No. 08/514,806, filed on Oct. 31, 1995; which is a continuation-in part application of Ser. No.08/269,139, filed Jun. 30, 1994, now U.S. Pat. No. 5,460,627, issuing on Oct. 24, 1995; which is a continuation-in-part of Ser. No. 08/055,578, filed May 3, 1993 abandoned.

BACKGROUND OF THE INVENTION

This invention relates generally to the evaluation of a laser used in ophthalmologic surgery and, more specifically, to a test substrate on which test ablations are performed to evaluate the laser.

Ultraviolet (UV) laser evaluation and calibration typically has been done on a flat substrate of polymethylmethacrylate (PMMA) which is then read on a lensometer to confirm the laser calibration. In my U.S. Pat. No. 5,460,627 I disclose the use of a rastostereographic or placido-disc corneal topographic analysis of a test substrate to enhance the calibration process. Such technologies enhance the calibration process by providing additional information beyond the means of a lensometer. Further, my co-pending application Ser. No. 08/514,806, filed Aug. 14, 1995, further provides for improvements in the above technologies.

Rastostereographs or rastophotogrammetry has been used in opththalmological surgery to measure the surface contour of the optic nerve head and to measure corneal surface curvatures. In the technique of rastophotogrammetry a series of parallel lines or a grid is projected on the surface to be measured. Computerized digital analysis of a video image is performed to detect elevations or depressions of the surface being measured. Rastostereographic imaging is combined with image processing computer software to produce the topography of the cornea, for example.

Recently is has been determined that placido-disc videokeratoscopy can be used to determine surface contour, particularly to visualize and determine the surface contour of a contact lens or artificial cornea. The placido-disc video keratoscope is a type of computerized videokeratography now available to ophthalmologic surgeons. The instrument allows the surgeon to measure and modify corneal curvature. The basic videokeratograph instrument includes a light source projected onto the cornea. The modification of the light by the cornea is captured by a video camera and the information is analyzed by computer software. The data is displayed in a variety of formats including photographs and on a screen.

As stated above, the rastophotogram and placido-disc technologies have been used to analyze a test substrate, rather than the cornea, to evaluate the ablating effect of a surgical laser. And while these technologies enhance the calibration process, they are still limited by the relative inefficiency of UV lasers to ablate test substrates, as opposed to the human cornea. For example, a minus four (4) diopter ablation in cornea can result in as little as one (1) diopter ablation in PMMA. Such a small correction makes it even more difficult to detect calibration error. Specifically, a 2% error would only be 0.24 microns of central ablation depth for a 6 mm ablation zone diameter in PMMA. It would be advantageous, therefore, to have a substrate that more closely resembled the human cornea upon ablation so as to give a more accurate prediction of laser effect.

SUMMARY OF THE INVENTION

It is among the principal objects of the present invention to provide a target substrate for the evaluation of a surgical laser.

It is another object of the invention to provide such a substrate that ablates in a manner similar to human corneal tissue.

Still another object of the invention is to provide such a substrate that can be analyzed pre-ablation and post-ablation so as to allow evaluation of the ablating laser.

Yet another object of the invention is to provide such a substrate that can be analyzed with a lensometer, rastophotogrammetry or placido-disc videokeratoscopy to give an accurate evaluation of the ablative power of the surgical laser.

Another object of the invention to provide a method of confirming the desired lens effect of a laser beam on a target substrate.

In accordance with the invention, generally stated, as target substrate is provided that is more efficiently ablated that PMMA or other known substrates and has characteristics more nearly those of human cornea in response to laser energy. The substrate is, in one preferred embodiment, an anhydrous substances including acrylic, silicone. Further, inorganic or organic gels such as cross-linked collagen can be used. The substrates are relatively devoid of water and homogeneous.

The topography of the novel target substrate can be analyzed by rastostereogrammetry, rastophotogrammetry, placido-disc videokeratoscopy, lensometry or other technologies. A test ablation is performed on the substrate. The topographical analysis is repeated. The surgeon can use a comparison of the two topographical analyses to evaluate the laser's effect on human cornea prior to a surgical procedure.

BRIEF DESCRIPTION OF THE DRAWINGS

FIG. 1 is a diagram illustrating the use of rastophotogrammetry to determine unwanted lens effect (i.e. hot or cold spots) of a laser beam;

FIG. 2 is a diagram illustrating the use of rastophotogrammetry to confirm the desired lens effect of a laser beam;

FIG. 3 is a diagram illustrating the use of rastophotogrammetry in an ophthalmologic surgical procedure;

FIG. 4A is a diagram illustrating the use of rastophotogrammetry to evaluate a laser based on the effect on a contact lens of a known refractive power;

DESCRIPTION OF THE PREFERRED EMBODIMENT

Figure 4B:
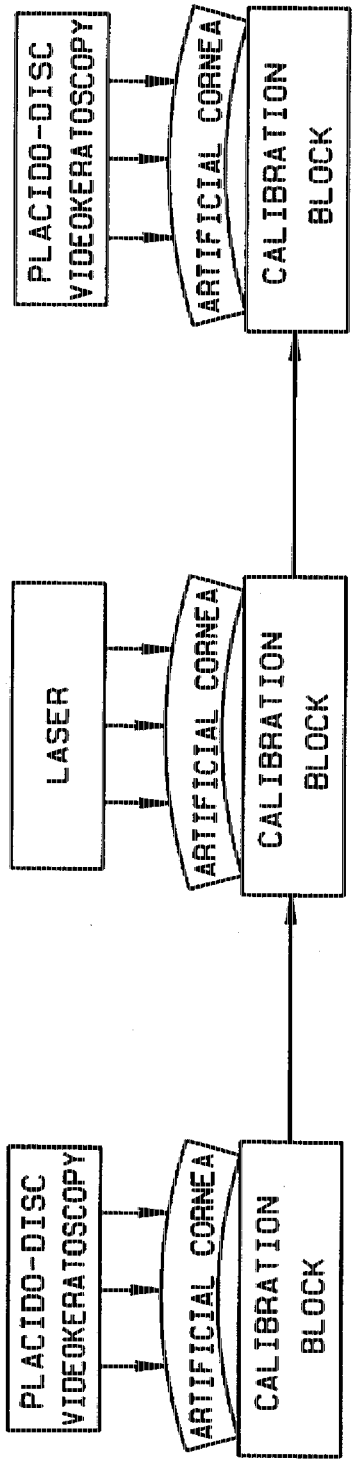
FIG. 4B is a diagram illustrating the use of placido-disc videokeratoscopy to evaluate a laser based on the effect on an artificial cornea of a known refractive power.

As illustrated in FIG. 1, rastophotogrammetry is used to determine the amount of unwanted lens effect delivered by an excimer or other ultraviolet or infrared laser beam. Rastophotogrammetry devices used in these procedures are the type marketed by PAR Technology Corp., Hartford, N.Y. 13413. A calibration block, typically made of polymethylmethacrylate (PMMA) is employed, in one embodiment. However, improved target substrates, which are the subject of the instant invention, may be used, as will be explained in detail below. The rastophotogrammetry is used before calibration to evaluate the ablative effects of the laser beam. A rastophotogram is made of the calibration block, the laser energy is applied to the calibration block and, a second rastophotogram is made to see if the laser effect is a uniform ablation with no depressions (hot spots) or elevations (cold spots). A shown in FIG. 1, the rastophotogram confirms a uniform and accurate ablation of the calibration block.

Confirmation of a desired lens effect is illustrated in FIG. 2. A rastophotogram is made of a target substrate, i.e. a calibration block. The laser beam is applied to the calibration block, and a second rastophotogram is performed to confirm the desired lens effect in the calibration block. For example, the desired lens effect is 4.00 dioptric, the amount of calibration block material that is removed at each point along the radius of the calibration block can be computed and the actual amount removed compared quantitatively and qualitatively to the effect desired. Moreover, the astigmatic and multizone (asphericity) correction desired can be calibrated and measured quantitatively.

FIG. 3 illustrates the use of rastophotogrammetry in corneal surgery performed to alter the refractive power of the human cornea. As illustrated, a rastophotogram is made of a calibration block. As previously stated, the laser is applied to the calibration block to determine when or not there is unwanted lens effect. In this manner and through these steps it can be evaluated whether the laser is properly calibrated before the laser is used on the human eye. Next, a rastophotogram is performed on a deepithelialized human cornea. The laser then is applied to the deepithelialized cornea and ablation performed. Finally, rastophotogrammetry is performed to determine if the proper shape (refractive power) of the deepithelialized cornea has been achieved. The steps may be repeated to validate repeated ablations.

As illustrated in FIG. 3, under-correction can be avoided by continuing the treatment session until the desired amount of correction is achieved. Furthermore, in order to enhance the quality of the photo image at this point, a surface dye can be applied to the deepithelialized cornea. In addition, the rastophotogrammetry grid can be projected using various wave lengths and filters for optimal visualization of the projected grid.

FIG. 4A illustrates the use of rastophotogrammetry in the evaluation of the surgical laser using a target substrate formed as a contact lens of a known dioptric power. A contact lens of a known dioptric power from PMMA is fastened to a holding block. The contact lens can be white to facilitate imaging with the rastophotogrammetric system. Alternatively, it can be impregnated with a fluorescein dye. Next, rastophotogrammetry is performed on the contact lens front surface to get an accurate baseline reading of the topography of the front surface of the lens. Next, the laser is used on the front surface of the lens. Finally, a second rastophotogram is performed to determine that the effect of the laser on the lens results in the desired change in the known dioptric power of the lens so that the laser can be calibrated properly based upon the evaluation of the effect of the laser on a lens with known dioptric power. The steps in the procedure may be repeated to validate the calibration.

FIG. 4B illustrates the use of placido-disc videokeratoscopy in the evaluation of the ablative effects of a surgical laser using an artificial cornea of a known dioptric power formed from PMMA or other appropriate material, as will be described below relative to the instant invention. The artificial cornea is fastened to a holding block, as previously described. The artificial cornea can be black plastic to facilitate imaging with a videokeratoscope. The artificial cornea should be colored all the way through so that ablation does not penetrate only a colored layer.

Next, a placido-disc videokeratoscope procedure is performed on the artificial cornea front surface to get an accurate baseline reading of the topography of the front surface. A first videokeratograph of the topography is made. Next, a laser is used on the front surface of the artificial cornea. A nonviscous, fine hydrophobic lubricant, such as a thin oil, can be placed on the ablated surface of the artificial cornea to enhance visualization since the ablated surface can lose its reflectivity. A second placido-disc videoscope procedure is performed and a second videokeratograph is made. The first and second videokeratographs are compared to evaluate the ablative effective of the laser.

It will be appreciated by those skilled in the art that placido-disc videokeratoscopic procedures work poorly on deepithelialized cornea right after surgery. However, the procedure works well for imaging the artificial cornea or other target substrates before and after an ablation, as first described. Therefore, the placido-disc can be used in connection with rastophotogrammetry in the surgical setting. The effect of laser on an artificial cornea can be determined by the use of placido-disc videokeratoscopy. The laser is used to perform corneal ablation. Subsequently, rastophotogrammetry is performed on the deepithelialized cornea to determine corneal topography. Corneal ablation is performed and a repeat rastophotogram is made and compared to the first to validate the laser effect.

Figure 5:
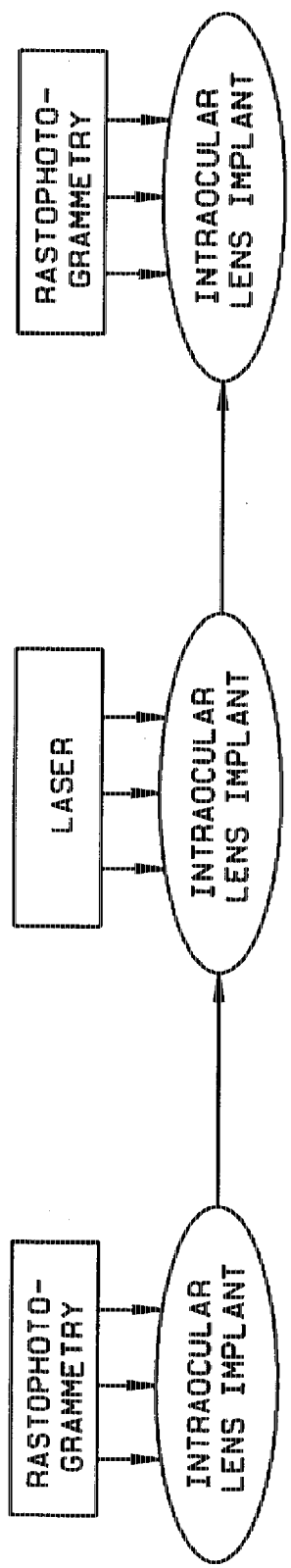
FIG. 5 is a diagram illustrating the use of rastophotogrammetry to change the refractive power of an intraocular implant.

FIG. 5 illustrates the use of the rastophotogram to determine the effective laser adjustment of refractive power of an intraocular lens implant. As illustrated, the rastophotogrammetry procedure is performed on the intraocular implant so as to determine a baseline. Next, the laser beam is applied to the intraocular lens implant to alter the curvature of the implant and thereby alter the refractive power. The second rastophotogram of the intraocular implant is then made to provide a feedback mechanism to ascertain if the desired refractive change has been made. The procedure may be repeated until the desired change in refractive power is achieved.

Figure 6:
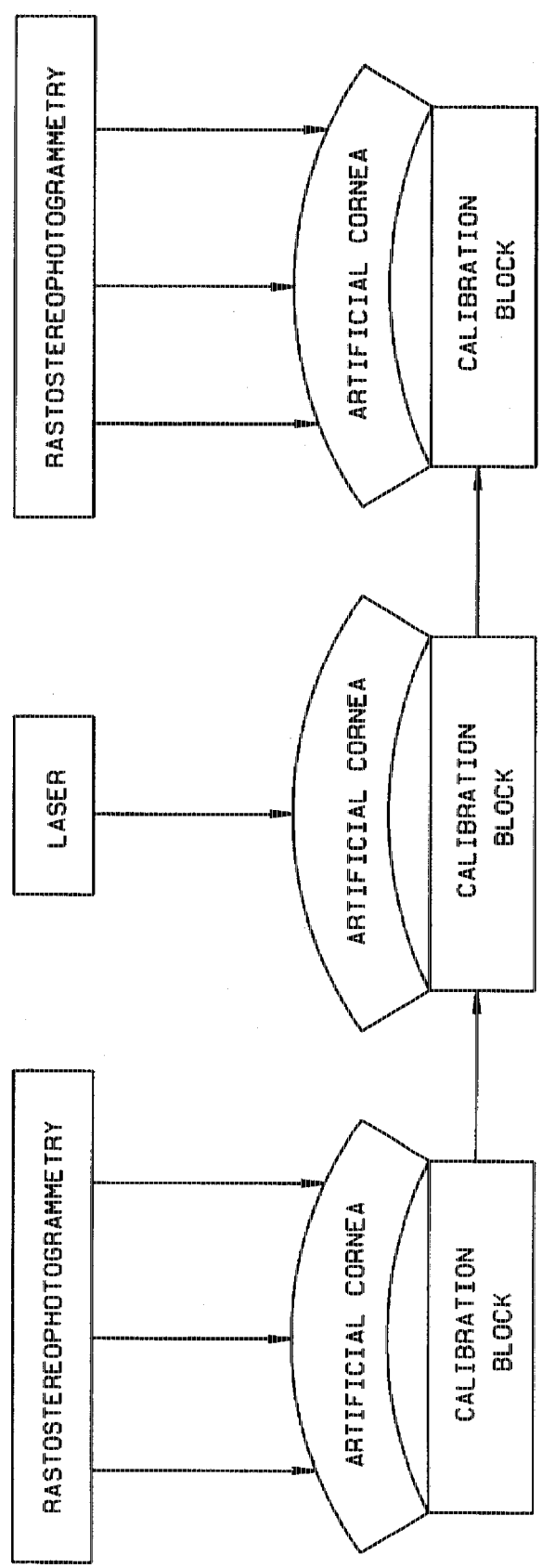
FIG. 6 is a diagram illustrating use of rastostereophotogrammetry to evaluate the effect of a laser on an artificial cornea of a know refractive power.

FIG. 6 illustrates the use of rastostereophotogrammetry, in addition to rastophotogrammetry, in the evaluation of a surgical laser using an artificial cornea of a known dioptric power. An artificial cornea of a known dioptric power formed from PMMA or other materials, as will be described below, is fastened to a holding block, as previously described. The artificial cornea can be white or fluorescein-impregnated, all the way through, to facilitate the imaging with the laser.

Following this, the rastostereophotogrammetry procedure is performed on the artificial cornea front surface to get an accurate baseline reading of the topography of the front surface of the artificial cornea. A first rastostereophotogram of the topography is made. Next, a laser is used on the present curvature of the artificial cornea. A rastophotogrammetry procedure is performed and a second image is made. The first and second images are compared to evaluate the ablating power of the laser. This procedure works well for imaging the artificial cornea before and after ablation, as initially described. The rastostereophotogrammetry is used on the reflective, pre-ablated substrate and the rastophotogrammetry is performed on the ablated substrate.

Therefore, rastophotogrammetry is useful in this type of surgical setting. Rastostereophotogrammetry may be performed on the cornea before deepithelialization or the rastophotogrammetry is performed on the deepithelialized cornea to determine a preablation corneal topography. Corneal ablation is performed and a repeat rastophotogram is made and compared to the first to validate the laser effect. One again, the purpose of this procedure is to attain the desired change in the refractive power of the cornea.

Figure 7:
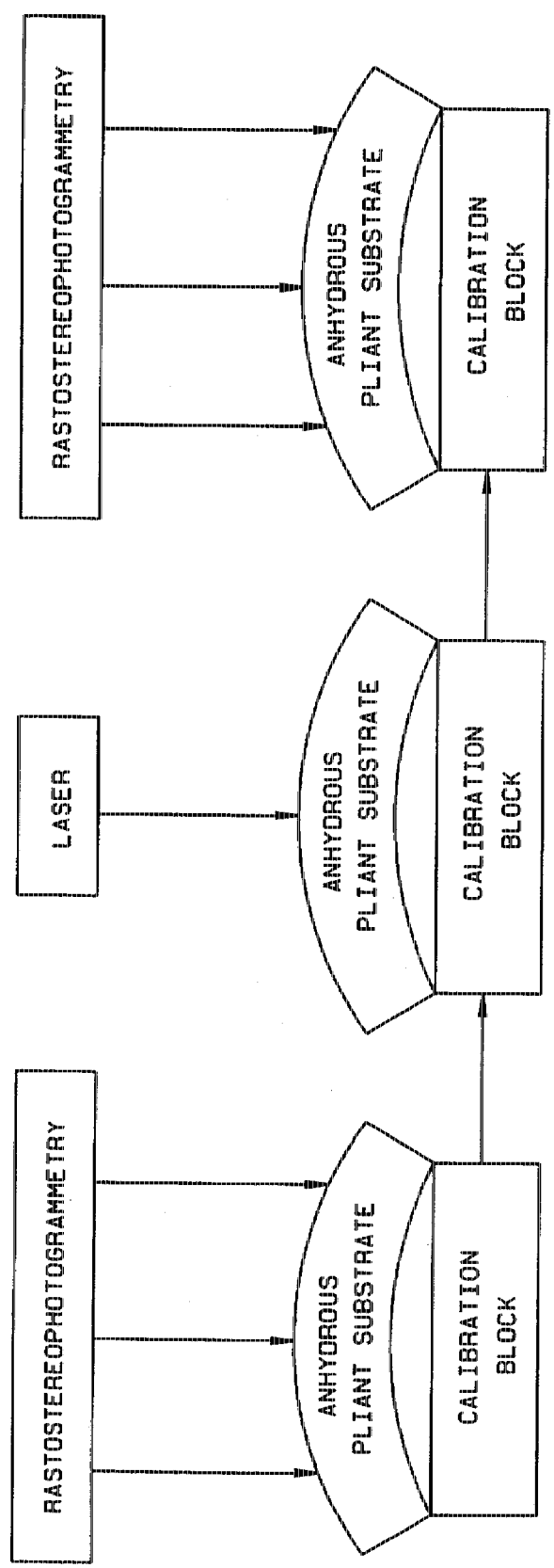
FIG. 7 is a diagram illustrating the use of rastostereophotogrammetry to evaluate the effect of a laser on an anhydrous pliant substrate of the present invention.

FIG. 7 illustrates the use of rastostereophotogrammetry, in addition to rastophotogrammetry, in the evaluation of a surgical laser using a novel, relatively anhydrous target substrate of the present invention. A novel target substrate is fastened to a holding block, as previously described. The target substrate is designed to be more efficiently ablated than a PMMA target substrate, lens implant or artificial cornea made from conventional materials, as previously described. Specifically, the target substrate is softer and ablates closer to the ablation rate of human corneal tissue. A simulated photorefractive keratectomy with an ultraviolet laser, for example as represented by the laser in the drawing, is used to very sensitively calibrate the laser. It generally is known that the human cornea typically ablates a rate that is dependent upon the laser's fluence. Further, the delivery system of the laser also effects the ablation rate for any given fluence. Specifically, a galvanometric delivery system that uses the purposeful, partial overlapping of adjacent pulses ablates human corneal tissue much more effectively than does a variable aperture (iris diaphragm) delivery system. Such a galvanometric delivery system is the subject matter of my co-pending application Ser. No.08/410,494, filed Mar. 24, 1995. For example, I have determined that for a fluence level of 160 to 180 mJ/cm$^2$ the galvanometric delivery system ablates cornea about 4.3 times more effectively that PMMA. In contrast, at this fluence, the variable aperture delivery systems ablate cornea about 1.4 to about 1.7 times more effectively that PMMA. That is why it is essential that the target substrate of FIG. 7 have characteristics similar to those of human corneal tissue.

It is generally known that water adversely effects ablation efficiency by absorbing UV energy. Therefore, the target substrate must have controlled water content for calibration purposes. Thus, the target substrate of the present invention is an anhydrous, pliant substrate softer that PMMA. Such substrates include acrylic and silicone. Moreover, any soft, water free plastic is contemplated by the scope of the invention. Further, formed inorganic or organic gels will perform better than PMMA. An examples of such a formed organic gel is a cross-linked collagen and derivatives.

The novel substrates are relatively devoid of water and homogeneous. Because they ablate at a rate that is closer to corneal ablation (i.e. 0.24 to 0.50 microns/pulse at a UV laser fluence of 160 to 180 mJ/cm$^2$), they are better suited than PMMA as a test substrate for laser calibration. In test ablations with a variable aperture system, acrylic ablated at 0.89 the rate of cornea. Thus, a –6 in cornea would be a –5.40 in acrylic. Also, a 6 mm ablation zone wherein 12 microns of central ablation depth represents one (1) diopter, a 2% error in acrylic represents 2% error of 72 microns, or 1.4 microns of central ablation depth, as opposed to as little as 0.96 micron in PMMA. Thus, the new target substrate represents approximately 50% increase in sensitivity as compared to PMMA.

It will be appreciated that the procedure of FIG. 7 is analogous to the procedure of FIG. 6 except for the use of the novel target substrate. Moreover, the novel target substrate of the present invention may be substituted for the calibration block, intraocular implant, artificial cornea or contact lens in any of the previously described procedures to give a more sensitive calibration and evaluation of the laser delivery service.

It will be appreciated by performing test ablations on the target substrate of the present invention will allow the surgeon to evaluate the effect the surgical laser will have on the human cornea. For example, the surgeon can perform a topographical analysis of the target substrate to determine the surface contour of the novel target substrate having ablative characteristics similar to those of the human cornea. Next, the surgeon can apply laser energy to the target substrate and perform a test ablation. Next, the surgeon can perform a second topographical analysis of the target substrate to determine the surface contour of the ablated target substrate. The surgeon then can compare the two surface substrates to evaluate the depth and area of ablation. In this manner the surgeon can evaluate the laser power, i.e. fluence produced by any given surgical laser and its effect on human cornea. The surgeon thus can modify his or her surgical technique in response to the evaluation.

It will be appreciated that the surgeon may use any of the illustrated or described methods of topographical analysis including, but not limited to rastophotogrammetry, rastostereography, placido-disc imaging, conventional lensometry and so forth, without departing from the scope of the invention.

Various changes or modifications can be made in the foregoing description and accompanying drawings without departing from the scope of the appended claims. Therefore, the foregoing description and drawings are intended to be illustrative only and should not be viewed in a limiting sense.

I claim:

1. A test substrate for use in UV laser calibration comprising an anhydrous, homogeneous acrylic having an ablation rate that is essentially that of human corneal tissue, said test substrate subjected to test ablations to determine the effect of laser ablation prior to a surgery wherein said test ablations of the test substrate result in deeper ablations than previously known test substrates so as to allow for the detection of smaller errors in the laser ablation which occur at deeper ablations than detected with previously known test substrates thus allowing calibration of the UV laser.

2. A test substrate for use in calibration of a surgical laser comprising an anhydrous, homogeneous silicone that ablates at a rate and depth essentially that of human corneal tissue, said substrate designed to allow test ablations which result in deeper ablations than previously known test substrates so as to allow for the detection of smaller errors in the laser ablation which occur at deeper ablations than detected with previously known test substrates, said deeper test ablations used for calibration of the surgical laser.

3. A method of evaluating a surgical laser being scanned by a glavanometric delivery system at a fluence of about 160 to about 180 mJ/cm for use in ophthalmologic surgery comprising the steps of:

performing a first evaluation of a topography of a target substrate to determine a first surface contour of the target substrate, said target substrate of acrylic or silicone having laser ablating depth and rate essentially the same as a human cornea;

applying a laser beam to said target substrate;

ablating said target substrate with said laser beam, said laser beam being provided by a galvanometric delivery system at a fluence of about 160 to about 180 mJ/cm$^2$;

performing a second evaluation of the topography of the target substrate after ablation to determine a second surface contour of the target substrate;

comparing the first surface contour with the second surface contour; and estimating the effect of said laser beam on a human cornea based upon the comparison of the first and second surface contours.

* * * * *

UNITED STATES PATENT AND TRADEMARK OFFICE
CERTIFICATE OF CORRECTION

PATENT NO. : 5,713,893
DATED : February 3, 1998
INVENTOR(S) : Francis E. O'Donnell, Jr.

It is certified that error appears in the above-indentified patent and that said Letters Patent is hereby corrected as shown below:

Column 6, claim 2, lines 47-48, replace "that ablates at a rate and depth" with ---having an ablation rate that---.

Signed and Sealed this

Twenty-first Day of April, 1998

Attest:

BRUCE LEHMAN

Attesting Officer    Commissioner of Patents and Trademarks